United States Patent
Ghaeini et al.

(10) Patent No.: US 11,544,529 B2
(45) Date of Patent: Jan. 3, 2023

(54) SEMI-SUPERVISED CLASSIFICATION WITH STACKED AUTOENCODER

(71) Applicant: KONINKLIJKE PHILIPS N.V., Eindhoven (NL)

(72) Inventors: Reza Ghaeini, Malden, MA (US); Sheikh Sadid Al Hasan, Cambridge, MA (US); Oladimeji Feyisetan Farri, Yorktown Heights, NY (US); Kathy Lee, Westford, MA (US); Vivek Datla, Ashland, MA (US); Ashequl Qadir, Melrose, MA (US); Junyi Liu, Windham, NH (US); Aaditya Prakash, Waltham, MA (US)

(73) Assignee: Koninklijke Philips N.V., Eindhoven (NL)

( * ) Notice: Subject to any disclaimer, the term of this patent is extended or adjusted under 35 U.S.C. 154(b) by 972 days.

(21) Appl. No.: 16/329,959

(22) PCT Filed: Sep. 4, 2017

(86) PCT No.: PCT/EP2017/072037
§ 371 (c)(1),
(2) Date: Mar. 1, 2019

(87) PCT Pub. No.: WO2018/046412
PCT Pub. Date: Mar. 15, 2018

(65) Prior Publication Data
US 2019/0205733 A1    Jul. 4, 2019

Related U.S. Application Data

(60) Provisional application No. 62/384,250, filed on Sep. 7, 2016.

(51) Int. Cl.
*G06N 3/04*    (2006.01)
*G06N 3/08*    (2006.01)
(Continued)

(52) U.S. Cl.
CPC ......... *G06N 3/0454* (2013.01); *G06K 9/6267* (2013.01); *G06N 3/084* (2013.01); *G06N 3/088* (2013.01); *G16H 50/20* (2018.01)

(58) Field of Classification Search
CPC ........ G06N 3/0454; G06N 3/08; G06N 3/088; G06N 3/084; G06N 3/04; G06N 20/00; G06K 9/6267; G06K 9/62; G16H 50/20
See application file for complete search history.

(56) References Cited

PUBLICATIONS

Mikolov, T. et al., "Distributed Representations of Words and Phrases and their Compositionality". Oct. 16, 2013, XP055192737.
(Continued)

*Primary Examiner* — Tuan H Nguyen

(57) ABSTRACT

Techniques described herein relate to semi-supervised training and application of stacked autoencoders and other classifiers for predictive and other purposes. In various embodiments, a semi-supervised model (108) may be trained for sentence classification, and may combine what is referred to herein as a "residual stacked de-noising autoencoder" ("RSDA") (220), which may be unsupervised, with a supervised classifier (218) such as a classification neural network (e.g., a multilayer perceptron, or "MLP"). In various embodiments, the RSDA may be a stacked denoising autoencoder that may or may not include one or more residual connections. If present, the residual connections may help the RSDA "remember" forgotten information across multiple layers. In various embodiments, the semi-supervised model may be trained with unlabeled data (for the RSDA) and labeled data (for the classifier) simultaneously.

21 Claims, 7 Drawing Sheets

(51) Int. Cl.
    *G16H 50/20*        (2018.01)
    *G06K 9/62*         (2022.01)

(56)            References Cited

PUBLICATIONS

Pennington, J. et al., "Glove: Global vectors fro word representation", Proceedings of the 2014 Conference on Empirical Methods in Natural Language Processing (EMNLP), Oct. 25-29, 2014, Doha, Qatar, Oct. 2014, pp. 1532-1543.

Glorot, et al., "Domain Adaptation for Large-Scale Sentiment Classification: A Deep Learning Approach", ICML'11 Proceedings of the 28th International Conference on International, Jan. 1, 2011, pp. 513-520.

Zhou, et al., "Cross-lingual sentiment classification with stacked autoencoders", Knowledge and Information Systems, Springer Verlag, London, GB, vol. 47, No. 1, Jun. 11, 2015, pp. 27-44.

Vincent, et al., "Stacked Denoising Autoencoders: Learning Useful Representations in a Deep Network with a Local Denoising Criterion", Journal of Machine Learning Research, 11, 2010, pp. 3371-3408.

Gehring, et al., "Extracting Deep Bottleneck Features Using Stacked Auto-Encoders", 2013 IEEE International Conference on Acoustics, Speech and Signal Processing (ICASSP), Vancouver, BC; Institute of Electrical and Electronics Engineers, Piscataway, NJ, US, May 26, 2013, pp. 3377-3381.

Anonymous, "Stacked Autoencoders ufldl", Apr. 7, 2013, Retrieved from the Internet:URL:http://deeplearning.stanford.edu/wi ki/index.php/Stacked_Autoencoders, 5 pages (Abstract).

Kiros, et al., "Skip-Thought Vectors", Jun. 22, 2015, Retrieved from the Internet:URL:https://arxiv.org/pdf/1506.06726.pdf, pp. 1-11 (Abstract).

SEMI-SUPERVISED CLASSIFICATION WITH STACKED AUTOENCODER

CROSS-REFERENCE TO PRIOR APPLICATIONS

This application is the U.S. National Phase application under 35 U.S.C. § 371 of International Application No. PCT/EP2017/072037, filed on Sep. 4, 2017, which claims the benefit of Provisional Application Ser. No. 62/384,250, filed Sep. 7, 2016. These applications are hereby incorporated by reference herein, for all purposes.

TECHNICAL FIELD

Various embodiments described herein are directed generally to artificial intelligence. More particularly, but not exclusively, various methods and apparatus disclosed herein relate to semi-supervised training and application of stacked autoencoders and other classifiers for predictive and other purposes.

BACKGROUND

Deep learning-based methods for classification typically rely on massive amounts of labeled data. However, acquiring labeled data is costly, and this limits researchers from applying these techniques to many natural language processing tasks. Current semi-supervised methods for deep learning mainly use unlabeled data for learning word embeddings, which are then used in supervised classification, but these learned vectors do not directly benefit from supervision. Semi-supervised learning aims to improve the performance of supervised approaches by leveraging both unlabeled and labeled data. There have been some limited attempts to use deep learning for semi-supervised sentence classification, e.g., using convolutional neural networks ("CNNs") and/or long short-term memory networks ("LSTMs") to learn word embeddings from unlabeled training data and then utilizing these embeddings for supervised classification. While such efforts may alleviate some error in sentence classification tasks, there remain two major limitations. First, these methods have so far only focused on the simple scenario of single sentence classification. Second, such attempts have mainly involved using unlabeled data for word embeddings extraction, followed by supervised classification in a pipeline setting. Consequently, they are unable to learn discriminatory features from both unlabeled and labeled data jointly.

SUMMARY

The present disclosure is directed to methods and apparatus for semi-supervised training and application of stacked autoencoders and other classifiers/models for predictive and other purposes. For example, described herein is a semi-supervised model for sentence classification that combines what is referred to herein as a "residual stacked de-noising autoencoder" ("RSDA"), which may be unsupervised, with a supervised classifier such as a classification neural network (e.g., a multilayer perceptron, or "MLP"). In various embodiments, the RSDA may be a stacked de-noising autoencoder that may or may not include one or more residual connections. If present, the residual connections may help the RSDA "remember" forgotten information across multiple layers. In various embodiments, the semi-supervised model may be trained with unlabeled data (for the RSDA) and labeled data (for the classifier) simultaneously.

Once trained, one or more portions of the semi-supervised model may be used for a variety of classification tasks, including but not limited to paraphrase identification, sentiment detection (e.g., of movie reviews, music reviews, book reviews, product reviews, etc.), subjectivity classification, and sentence entailment. For example, in some embodiments, one or more decoder layers of the autoencoder may be discarded (or ignored) after the RSDA is trained. One or more remaining encoder layers of the RSDA may be used to generate encoded embeddings, e.g., of sentence embeddings, that may be applied as input to the classifier (e.g., across a classification neural network) to predict one or more labels associated with one or more of the aforementioned classification tasks. While techniques described herein are usable to predict labels in any number of domains, some embodiments described herein are related to predicting diagnoses and/or other outcomes from free form clinical notes.

Generally, in one aspect, a method may include: applying, as unlabeled training data across an embedding machine learning model, a first plurality of sentences to generate a plurality of sentence embeddings; applying, as input across an autoencoder machine learning model, the plurality of sentence embeddings to train the autoencoder machine learning model, wherein the autoencoder machine learning model includes one or more encoder layers and one or more decoder layers; applying, as labeled training data across one or more instances of an encoder machine learning model, a second plurality of sentences to generate a plurality of encoded embeddings, wherein the second plurality of sentences are associated with a corresponding plurality of labels, and wherein the encoder machine learning model includes the one or more encoder layers of the autoencoder machine learning model; applying, as labeled training data across a classifier, the plurality of encoded embeddings to generate output; and training the classifier based on the output and the plurality of labels to classify subsequent sentences with one or more of the plurality of labels.

In various embodiments, the embedding machine learning model may include a skip-thoughts model. In various embodiments, the one or more encoder layers may include a sequence of multiple encoder layers, and the one or more decoder layers comprise a sequence of multiple decoder layers that mirror the sequence of multiple encoder layers. In various embodiments, the autoencoder machine learning model may include one or more residual connections. In various embodiments, the one or more residual connections may include a residual connection between a last encoder layer of the sequence of multiple encoder layers and a last decoder layer of the sequence of multiple decoder layers.

In various embodiments, the embedding machine learning model may include a convolutional neural network. In various embodiments, the classifier may include a multilayer perceptron and a softmax layer. In various embodiments, the first and second plurality of sentences may include free form clinical notes, and the plurality of labels include a plurality of diagnoses associated with the free form clinical notes.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

DETAILED DESCRIPTION

Deep learning-based methods for classification typically rely on massive amounts of labeled data. However, acquiring labeled data is costly, and this limits researchers from applying these techniques to many natural language processing tasks. Current semi-supervised methods for deep learning mainly use unlabeled data for learning word embeddings, and then use the word embeddings for supervised classification, but these learned vectors do not directly benefit from supervision. Semi-supervised learning aims to improve the performance of supervised approaches by leveraging both unlabeled and labeled data. There have been some limited attempts to use deep learning for semi-supervised sentence classification, e.g., using convolutional neural networks ("CNNs") and/or long short-term memory networks ("LSTMs") to learn word embeddings from unlabeled training data and then utilize these embeddings for supervised classification. While such efforts may alleviate some error in sentence classification tasks, there remain two major limitations. First, these methods have so far only focused on the simple scenario of single sentence classification. Second, such attempts have mainly involved using unlabeled data for word embeddings extraction, followed by supervised classification in a pipeline setting. Consequently, they are unable to learn discriminatory features from both unlabeled and labeled data jointly. In view of the foregoing, various embodiments and implementations of the present disclosure are directed to semi-supervised training and application of stacked autoencoders and other classifiers for predictive and other purposes.

Figure 1:
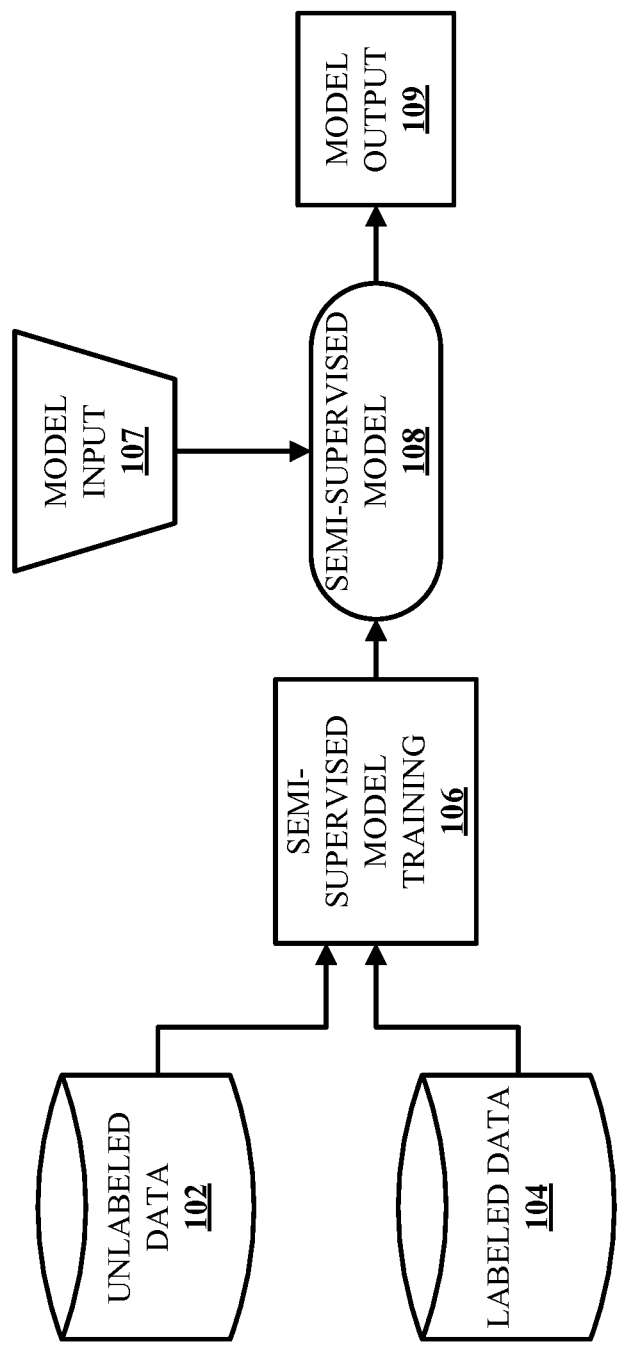
FIG. 1 schematically illustrates, at a high level, how various components may interact in accordance with various embodiments.

FIG. 1 schematically illustrates, at a high level, how various components may interact in accordance with various embodiments. Both unlabeled data 102 and labeled data 104 are used at block 106 to train a semi-supervised model 108. It should be understood that the descriptor "semi-supervised" when applied to "model" herein merely refers to how the model was trained, and does not necessarily imply additional supervision once the model is applied to subsequent data to make predictions. Once semi-supervised model 108 is trained, model input 107 may be applied to (e.g., across) semi-supervised model 108 to generate model output 109.

Model output 109 may include a variety of different types of data depending on the data on which semi-supervised model 108 was trained and/or model input 107, such as predictions of various labels or classifications, whether a sentence is a paraphrase of another sentence, a sentiment of one or more sentences, and so forth. For example, in some embodiments, semi-supervised model 108 may be trained using labeled and unlabeled free form clinical notes that include, for instance, observations about patients such as symptoms, labs, treatments, orders, etc. Once trained, an unlabeled free-form clinical note associated with a particular patient may be applied as input 107 across semi-supervised model 108 to generate model output 109 that includes, for instance, one or more diagnostic predictions associated with the particular patient.

Figure 2:
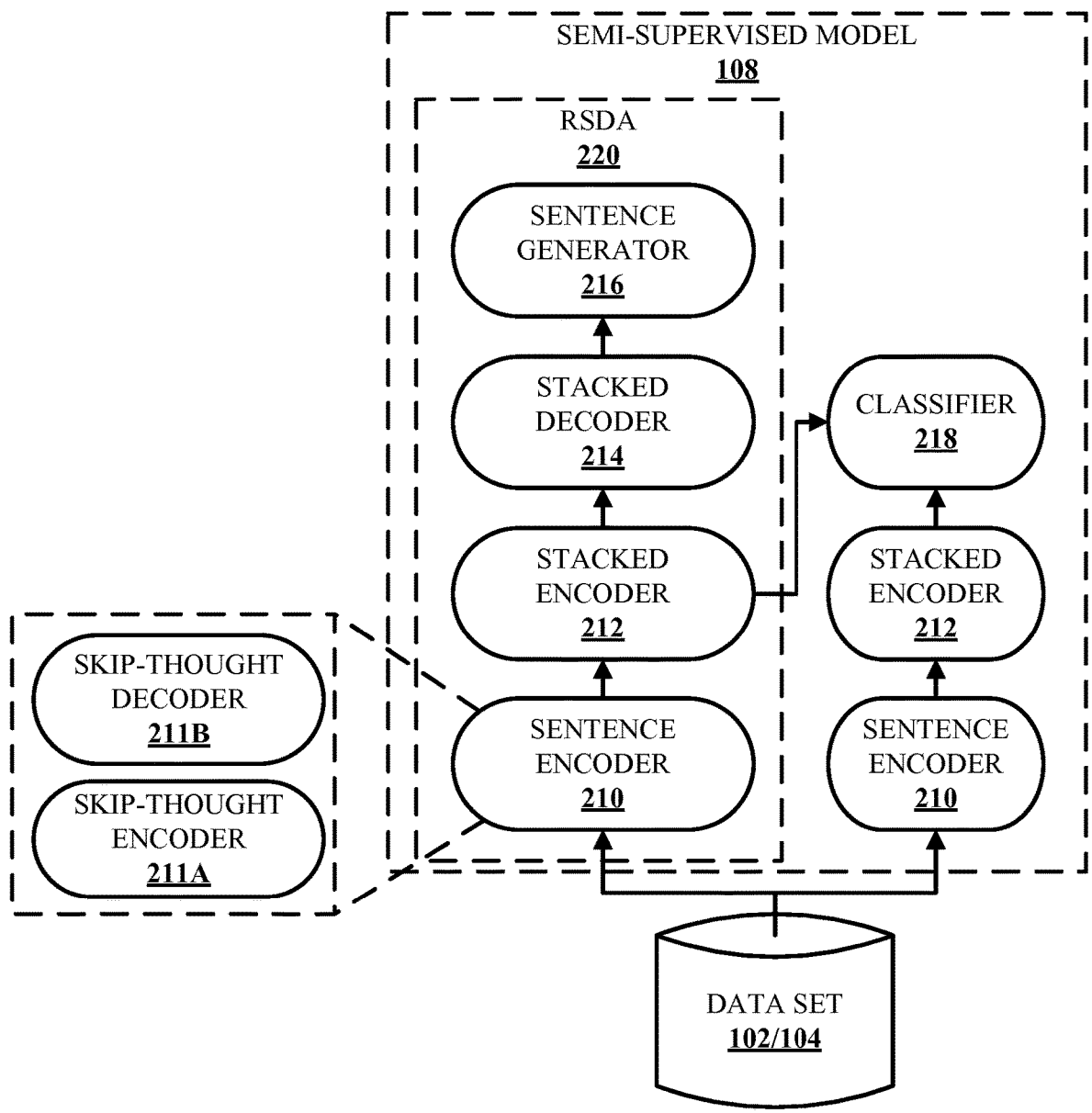
FIG. 2 schematically illustrates, with slightly more detail than FIG. 1, how various components described herein may interact, in accordance with various embodiments.

FIG. 2 schematically illustrates, in more detail than FIG. 1, a view of components of semi-supervised model 108. In FIG. 2, semi-supervised model 108 includes an RSDA 220 (which is unsupervised—trained using unlabeled data 102) and a classifier 218 (which is supervised—trained using labeled data 104). RSDA 220 may include a sentence decoder 210, one or more encoder layers that are referred to in FIG. 2 as a "stacked encoder" 212, one or more decoder layers that are referred to in FIG. 2 as a "stacked decoder" 214, and a sentence generator 216. More generally, trained model 108 may include RSDA 220 (particularly sentence encoder 210 and stacked encoder 212), classifier 218, and, in addition, another instance of sentence encoder 210 and stacked encoder 212 that feed into classifier 218. The instances of sentence encoder 210 and stacked encoder 212 on the right in FIG. 2 may be identical to those on the left-hand side once those on the left hand side (i.e. share weights) are trained.

In various embodiments, sentence encoder 210 may be configured to generate, based on input of one or more sentences or sequences of words, sentence embeddings—i.e., fixed-length vector representations that contain valuable information at the sentence level—using various techniques. In some embodiments, sentence encoder 210 may take the form of a trained skip-thought model that includes a recursive neural network ("RNN") encoder with gated recurrent unit ("GRU") activation and an RNN decoder with a conditional GRU. Such a model may be trained on various datasets, such as online corpuses of books. In some embodiments, sentence encoder 210 may be trained such that, given a triple of contiguous sentences $(s_i-1, s_i, s_i+1)$, sentence encoder 210 attempts to encode a sentence $s_i$ in a way to generate the previous sentence $(s_i-1)$ and the following sentence $(s_i+1)$.

In various embodiments, sentence encoder 210 may include a skip-thought encoder 211A, a skip-thought decoder 211B, and an objective function (not depicted in FIG. 2). For the skip-thought encoder 211A, let $(w_i^1, w_i^2, \ldots, w_i^N)$ and $(x_i^1, x_i^2, \ldots, x_i^N)$ represent the words and word embeddings, respectively, in a sentence $s_i$, where N is the number of words in sentence $s_i$. In various embodiments, the skip-thought encoder 211A of sentence encoder 210 may be formulated as follows:

$$r^t = \sigma(W_r x^t + U_r h^{t-1}) \quad (1)$$

$$z^t = \sigma(W_z x^t + U_z h^{t-1}) \quad (2)$$

$$\bar{h}^t = \tanh(W x^t + U(r^t \odot h^{t-1})) \quad (3)$$

$$h^t = (1-z^t) \odot h^{t-1} + z^t \odot \bar{h}^t \quad (4)$$

wherein W and U represent different sets of weights, r is the reset gate, z is the update gate, $\bar{h}^t$ stands for the proposed state update at time t, $h^t$ is the output at time t, and $\odot$ denotes an element-wise product.

As noted above, the skip-thought decoder 211B of sentence encoder 210 may comprise a GRU that may be conditioned, for instance, on the encoder output, $h_i$. In various embodiments, the computation of the skip-thought decoder 211B of sentence encoder 210 may be similar to the skip-thought encoder 211A of sentence encoder 210, except that the skip-thought decoder 211B may include additional sets of weights, C, $C_r$, and $C_z$ to utilize encoder outputs in the GRU computations:

$$r^t = \sigma(W_r^d x^{t-1} + U_r^d h^{t-1} + C_r h_i) \quad (5)$$

$$z^t = \sigma(W_z^d x^{t-1} + U_z^d h^{t-1} + C_z h_i) \quad (6)$$

$$\bar{h}^t = \tanh(W^d x^{t-1} + U^d(r^t \odot h^{t-1}) + C h_i) \quad (7)$$

$$h^t = (1-z^t) \odot h^{t-1} + z^t \odot \bar{h}^t \quad (8)$$

The objective function associated with skip-thought encoder 211A and skip-thought decoder 211B may be the sum of the log-probabilities of the previous ($s_{i-1}$) and following ($s_{i+1}$) sentences conditioned on the encoded representation of the current ($s_i$) sentence, $h_i$:

$$\Sigma_t \log P(w_{i+1}^t | w_{i+1}^{<t}, h_i) + \Sigma_t \log P(w_{i-1}^t | w_{i-1}^{<t}, h_i) \quad (9)$$

Once the skip-thoughts sentence encoder 210 is trained, in various embodiments, skip-thought decoder 211B may be effectively discarded, as is common with autoencoders in general. Thereafter, skip-thought encoder 211A may effectively function as a lookup table that maps sequences of words (or sentences) to sequence of word embeddings. It is these sequence of word embeddings that may be provided as input to the remainder of RSDA 220, specifically to stacked encoder 212. While skip-thoughts is described herein as being used to generate sequence of words embeddings, this is not meant to be limiting. In various embodiments, other types of models, such as those associated with word2vec, may be employed instead.

Turning back to RSDA 220, in various embodiments, given a sentence, s, from dataset 102/104, a sentence embedding may be extracted using sentence encoder 210 (more specifically, skip-thought encoder 211A as a lookup table) and applied as input across stacked encoder 212. In some embodiments, noise may be injected at each layer of stacked encoder 212 before applying the activation function and passing the output to the next layer (described in more detail below). Each layer of stacked decoder 214 may reconstruct a noiseless output of a corresponding layer of stacked encoder 212. Sentence generator 216 may be configured to reconstruct the input sentences based on output from stacked decoder 214. To the extent the output from sentence generator 216 differs from the original input sentence s, various training techniques, such as back propagation, stochastic gradient descent, etc., may be employed to adjust various weights associated with stacked encoder 212 and stacked decoder 214 (and possibly sentence generator 216) to correct the error and train RSDA 220.

Figure 3:
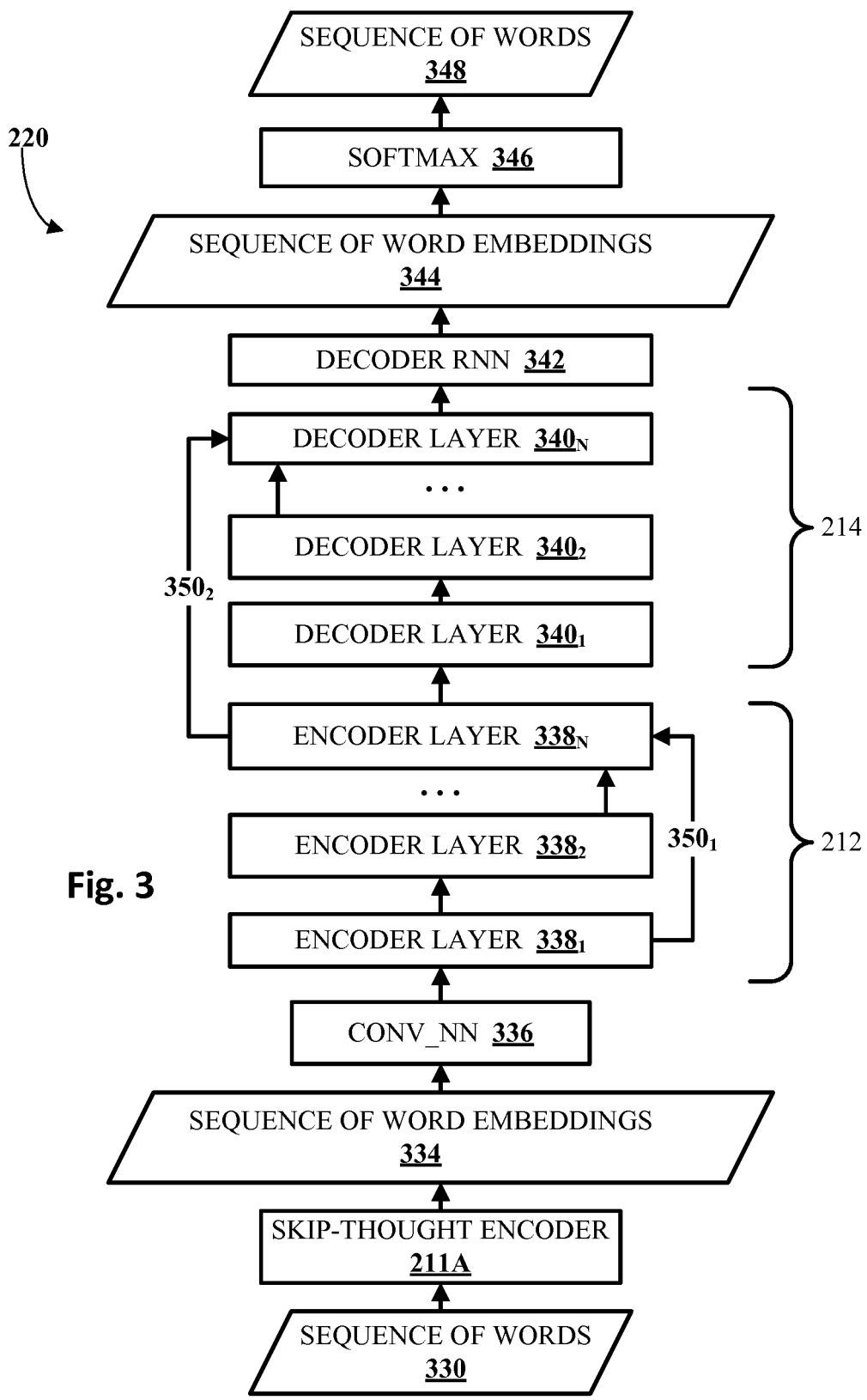
FIG. 3 schematically illustrates, in more detail than FIG. 1 or 2, one example of how an RSDA may be configured, in accordance with various embodiments.
Figure 4:
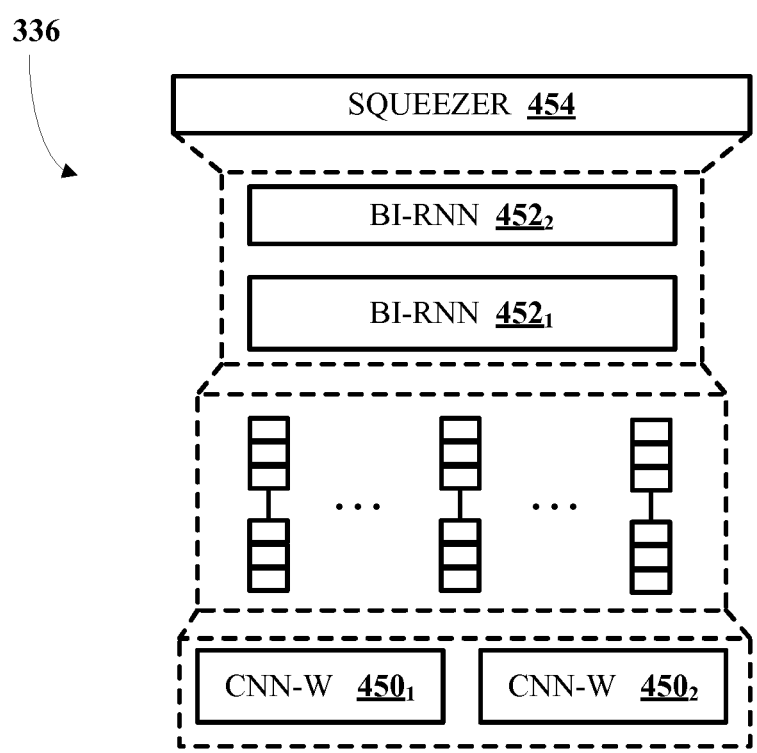
FIG. 4 depicts on example of a convolutional neural network architecture that may be employed, in accordance with various embodiments.

FIG. 3 schematically illustrates, in more detail than FIG. 2, one example of how an RSDA 220 may be configured, in accordance with various embodiments. In FIG. 3, a sequence of words 330, such as a sentence, may be applied as input across skip-thought encoder 211A as described above. The output of skip-thought encoder 211A is a sequence of word embeddings 334. In some embodiments, sequence of word embeddings 334 may be applied as input across one or more convolutional neural networks 336 to generate output, which in some embodiments may include encoded sequence of word embeddings. One example architecture for convolutional neural network 336 is depicted in FIG. 4 and described below.

Next, a sequence of one or more encoder layers $338_{1-N}$ (which corresponds to the stacked encoder 212 of FIG. 2) may be provided to receive the output generated by the convolutional neural network 336. As is typical with autoencoders, a sequence of one or more decoder layers $340_{1-N}$ (which correspond to the stacked decoder 214 of FIG. 2) may follow the sequence of encoder layers $338_{1-N}$. While three encoders and three decoders are depicted, this is not meant to be limiting; in various embodiments, more or less encoder and/or decoder layers may be employed.

After the decoder layers 340, in some embodiments, the output from the last decoder layer $340_N$ may be applied as input across a decoder recurrent neural network 342 to generate another sequence of word embeddings 344. The sequence of word embeddings 344 may then be passed to a softmax layer 346, which in turn may output a sequence of words 348. The goal may be to ensure that the sequence of words 348 are the same (i.e., reconstructed) as sequence of words 330. During training, to the extent the sequences of words 348, 330 are different, various optimization techniques such as back propagation, stochastic gradient descent, etc., may be employed to adjust weights associated with the various layers of RSDA 220.

In some embodiments, to improve the encoding and decoding process, one or more residual connections $350_{1-2}$ may be provided, e.g., at $350_1$ from first encoder layer $338_1$ to the last encoder layer $338_N$ (Encoded embedding) and/or at $350_2$ from the last encoder layer $338_N$ to the last decoder layer $340_N$ (Reconstructed embedding). Residual connections 350 may help the network to remember important information that otherwise may gradually dissipate across the multiple stacked layers. In some embodiments, when there is a residual connection 350 in a layer, input into this layer may be concatenated with the corresponding layer output (of the residual connection) and the previous layer output. The residual connections depicted in FIG. 3 are examples only; more, less, and/or different residual connections may be employed between various layers.

In some embodiments, RSDA 220 may be mathematically formulated as follows:

$$\bar{h}_l = W_l h_{l-1} \quad (10)$$

$$\hat{h}_l = \bar{h}_l + \mathcal{N}(0, \sigma^2) \quad (11)$$

$$h_l = \phi(\hat{h}_l) \quad (12)$$

where $\phi$ is the activation and $h_{l-1}$ is the input of layer l, which is the concatenation of two different layer outputs when there is a residual connection in layer l, $\bar{h}_l$, $\hat{h}_l$, and $h_l$ are noiseless pre-activation, noisy pre-activation, and output of layer l, respectively. The value of $\sigma^2$ may be a hyperparameter of the model that can be selected manually, based on empirical data, automatically, etc.

Referring back to FIG. 2, the supervised component of trained model 108, classifier 218, may be a machine learning model such as a multi-layer perceptron ("MLP"), a naïve Bayes classifier, a k-nearest neighbor classifier, support vector machines, and so forth. In various embodiments, encoded sentence embeddings generated by one or more instances of (now trained) stacked encoder 212 may be applied across classifier 218 to generate one or more predicted labels. Classifier 218 may be used for a variety of classification tasks, including but not limited to such as classification of a single sentence (e.g. movie review sentiment detection) or classification of a pair of sentences (e.g. paraphrase detection).

In various embodiments, classifier 218 may be a one-layer classifier, although this is not required in all embodiments. For example, in some embodiments, a single-layer classifier may be formulated as follows:

$$\overline{h}_c = W_c x \quad (14)$$

$$\hat{h}_c = \overline{h}_c + \mathcal{N}(0, \sigma^2) \quad (15)$$

$$h_c = \phi(\hat{h}_c) \quad (16)$$

$$o_c = \frac{\sigma(W_o h_c)}{\sum \sigma(W_o h_c)} \quad (17)$$

wherein $o_c$ is the output of classifier 218.

With regard to objective functions, in some embodiments, RSDA 220 may use a square error at each decoder layer 340 of stacked decoder 214. In some embodiments, classifier 218 may be trained using cross entropy with L1 and L2 regularization on top of a softmax layer. Accordingly, the objective function of classifier 218 may be the weighted summation of the squared error and cross entropy with regularization terms such as the following:

$$\text{cost} = \Sigma_{i=N+1}^{N+M} \Sigma_{l=1}^{L} (\text{decoder}_i^{(l)} - \text{Correspond Encoder}_i^{(l)})^2 + \lambda(-\Sigma_{i=1}^{N} \log P(y_i = y_i^* | X_i) + \alpha ||W_s||_2^2 + \beta |W_s|) \quad (13)$$

where L is the number of layers in encoder and decoder, X represents classifier input, $W_s$ stands for weights of the softmax layer, $\lambda$, $\alpha$, and $\beta$ are the hyperparameters of the cost function that controls the effect of each term in the cost function.

FIG. 4 depicts one example of a convolutional neural network architecture that may be employed to generate input (e.g., encoded sequence of word embeddings) for stacked encoder 212, e.g., by convolutional neural network 336 in FIG. 3, in accordance with various embodiments. A pair of convolutional neural networks with W window sizes ("CNN-Ws"), $450_1$ and $450_2$, may each receive, as input, a sentence (i.e. a sequence of words). In various embodiments, CNN-Ws $450_1$ and $450_2$ may together generate, as output, a concatenation of each CNN-W's individual output. This concatenated data may be applied as input across a sequence of one or more bi-directional recursive neural networks ("BI-RNNs") $452_1$ and $452_2$. BI-RNNs $452_1$ and $452_2$ may, in turn, generate output that is more meaningful that perhaps the original input sentence. While two BI-RNNs are depicted in FIG. 4, it should be understood that a sequence or stack of any number of BI-RNNs may be employed.

In some embodiments, output generated by BI-RNNs $452_1$ and $452_2$ may be applied as input across what is sometimes referred to as a "squeezer" 454 to generate a vector representation (or embedding) of a sentence from a sequence of representations. In various embodiments, squeezer 454 may be applied to each feature of each representation over the sequence of outputs generated by BI-RNNs $452_1$ and $452_2$. In various embodiments, the function employed by squeezer may be, for instance, maximum, minimum, mean, last, etc.

Figure 5:
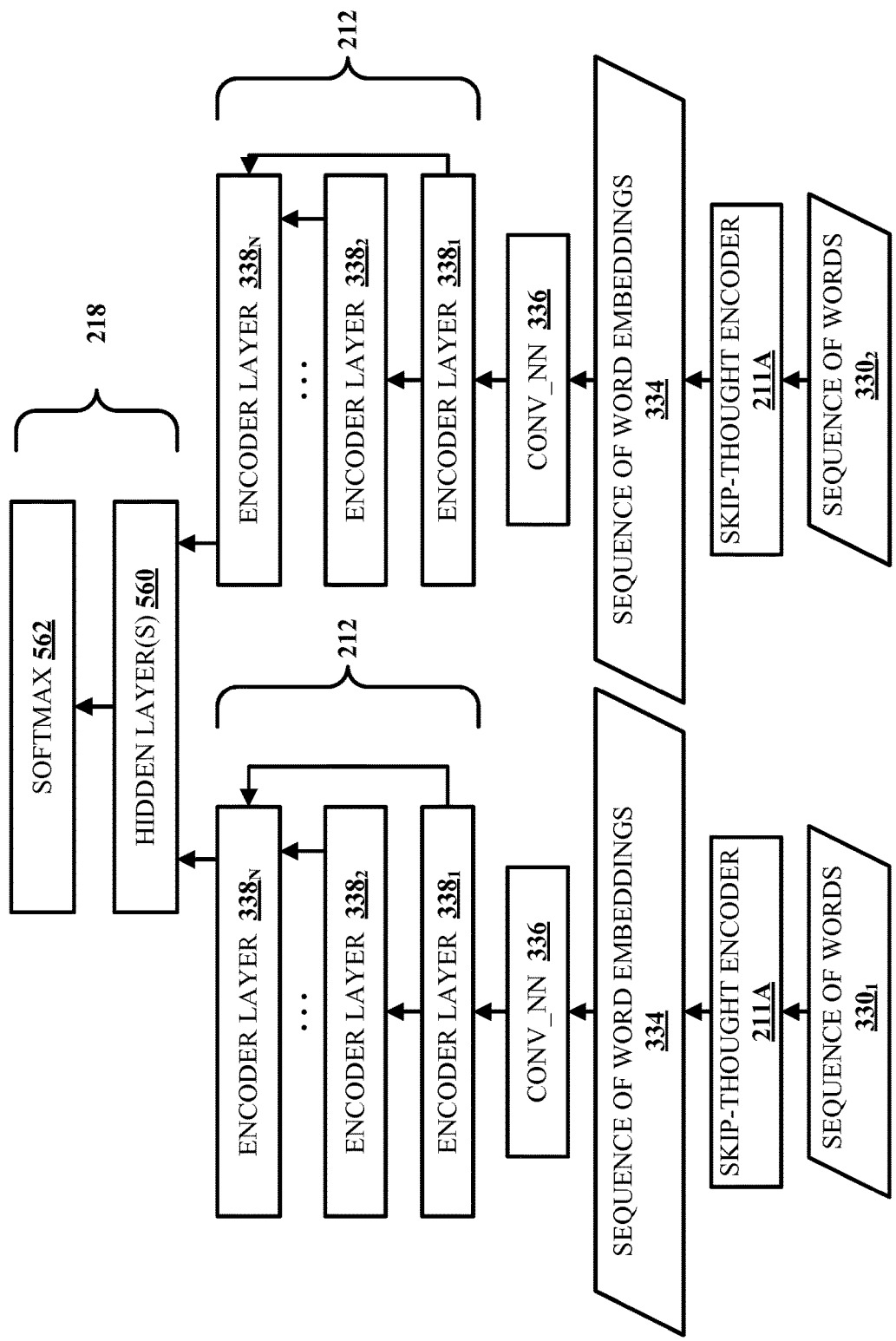
FIG. 5 depicts one example of how a trained semi-supervised model may be used to perform classification of sentence pairs, in accordance with various embodiments.

FIG. 5 depicts one example of how the stacked encoder 212 of FIG. 2, separated from stacked decoder 214, may be applied for paired classification, such as paraphrase detection, using two sentences as input. Given a pair of sentences (sequences of words), $330_1$ and $330_2$, sentence embeddings may be extracted using skip-thought encoder 211A (e.g., obtained from a pre-trained skip-thoughts model). Then, both extracted sentence embeddings may be applied as input across two stacked encoders 212 (which may share weights) to extract their encoded embeddings.

Classifier 218 takes the form of a fully-connected neural network that includes one or more hidden layers 560 and a softmax layer 562. A concatenation of encoder outputs (i.e., output from last encoder layer $338_N$) may be applied as input to classifier 218 to determine a conditional probability of each class given an input set: P(y|X), e.g., in accordance with equations (14)-(17) described above.

Figure 6:
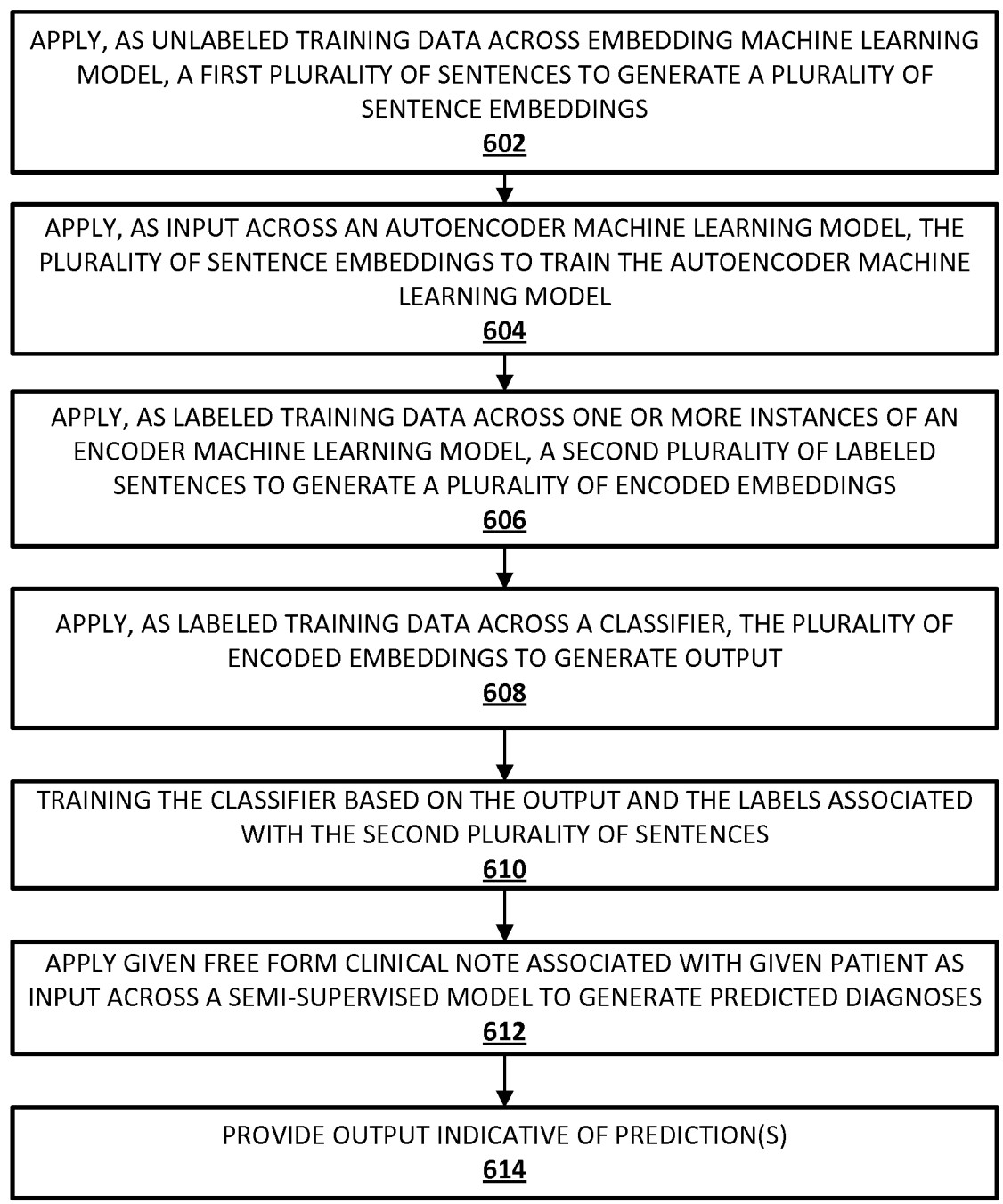
FIG. 6 depicts an example method for practicing selected aspects of the present disclosure, in accordance with various embodiments.

FIG. 6 depicts an example method 600 for practicing selected aspects of the present disclosure, in accordance with various embodiments. For convenience, the operations of the flow chart are described with reference to a system that performs the operations. This system may include various components of various computer systems, including 700. Moreover, while operations of method 600 are shown in a particular order, this is not meant to be limiting. One or more operations may be reordered, omitted or added.

At block 602, the system may apply, e.g., as unlabeled training data across a trained embedding machine learning model, a first plurality of sentences to generate a plurality of sequence of word embeddings (e.g., 334). As noted above, the embedding machine learning model may take various forms, such as a trained skip-thought model, such as skip-thought encoder 211A or a trained word2vec encoder.

At block 604, the system may apply, as input across an autoencoder machine learning model (e.g., RSDA 220), the plurality of sentence embeddings to train the autoencoder machine learning model. In various embodiments, the autoencoder machine learning model may include one or more encoder layers (e.g., $338_{1-N}$) and one or more decoder layers (e.g., $340_{1-N}$). While not depicted in FIG. 6, in some embodiments, the sequence of word embeddings may be applied as input across a convolutional neural network (e.g., 336) to generate encoded embeddings, and those encoded embeddings may be what is applied as input across the autoencoder machine learning model.

At block 606, the system may apply, e.g., as labeled training data across one or more instances of an encoder machine learning model (e.g., stacked encoder 212, including encoder layers $338_{1-N}$), a second plurality of sentences to generate a plurality of encoded embeddings. In various embodiments, the second plurality of sentences may be associated with a corresponding plurality of labels (e.g., diagnoses, predictions, classifications, etc.). As noted above, the encoder machine learning model may include the one or more encoder layers $338_{1-N}$ of RSDA 220, and the decoder layers $340_{1-N}$ may be discarded.

At block 608, the system may apply, as labeled training data across a classifier (e.g., 218), the plurality of encoded embeddings generated by the encoder machine learning model to generate output. In various embodiments, at block 610, this output may be used, e.g., along with the plurality of labels, to train the classifier (e.g., 218) to classify subsequent sentences with one or more of the plurality of labels.

Blocks 612-614 demonstrate optional operations that may be used in the clinical context to predict diagnoses. This is not meant to be limiting, and it should be understood that disclosed techniques may be used for a variety of additional purposes. At block 612, the system may apply a given free form clinical note associated with a given patient as input (e.g., 107) across a semi-supervised model (e.g., 108) to generate output (e.g., 109) that may, for instance, include one or more diagnoses predicted based on the given free form clinical note. As noted above, the semi-supervised model (e.g., 108) may include an unsupervised portion (e.g., encoder stack 212 of RSDA 220) and a supervised portion (e.g., classifier 218). In various embodiments, the aforementioned encoder machine learning model, which may include the stacked encoder 212 of RSDA 220 (e.g., with the stacked decoder 214 discarded after training), may feed into the classifier (e.g., 218) as depicted, for instance in FIG. 5.

At block 614, the system may provide output indicative of the one or more predictions generated at block 612. For example, in some embodiments, one or more predicted diagnoses (or outcomes) may be presented on a display device or on a report printed to paper. In some embodiments, one or more of the presented predicted diagnoses may include a probability that is determined based on the softmax functions described previously. In some embodiments, if the probability of a particular diagnosis satisfies a threshold, it may be presented more conspicuously than other diagnoses (e.g., bolded, in larger text, different color, etc.), and/or may trigger an alarm if the predicted diagnosis requires immediate attention. In some embodiments, the predicted diagnosis may be determined automatically, e.g., in response to a clinician filing an EHR in a hospital information system. In some such embodiments, the clinician may be informed of the predicted diagnoses on a display device, e.g., immediately or sometime later, e.g., through an email or other message means.

Table 1, below, depicts example results of applying techniques described herein using various parameters and/or by implementing selected aspects of the present disclosure in various ways, as compared to other techniques. The tests were performed with 500 and 1000 labeled samples, both with predefined development sets and test sets.

TABLE 1

| Model Name | 500 dev | 500 test | 1000 dev | 1000 test |
|---|---|---|---|---|
| Noiseless | 57.2 | 55.57 | 57 | 56.3 |
| InputNoise | 56.6 | 56.03 | 56.8 | 56.48 |
| EncoderNoise | 58.8 | 56.7 | 57.2 | 57.15 |
| DecoderNoise | 58.2 | 57.25 | 58 | 57.37 |
| FullNoise | 59.2 | 56.5 | 58 | 57.29 |
| RegResidual | 58.2 | 57.39 | 59 | 58.12 |
| L2Residual | 59 | 59.95 | 58.4 | 58.45 |
| NoRegResidual | 58.8 | 56.3 | 59.2 | 58.16 |
| LinearRes | 54.2 | 55.59 | 54.8 | 54.41 |
| ReLURes | 56.8 | 56.58 | 56.6 | 56.62 |
| SigmoisRes | 56.4 | 56.68 | 56.4 | 56.68 |
| SimpleIn | 54.6 | 52.46 | 55.2 | 54.67 |
| AugProdIn | 55.2 | 52.22 | 54.6 | 54.37 |
| AugAbsIn | 58.8 | 57.6 | 58.4 | 57.46 |
| AbsProdIn | 57.8 | 57.09 | 57.6 | 57.23 |

For design choice experiments, the learning rate was set to 0.01 and the models were trained for at most 400 epochs.

Noise testing started from a simple model without residual connection. Five different settings (shown in Table 1 above) were defined to investigate the effect of noise in all models. In all cases, noise is a random variable from $N(0; 0:5)$ distribution. In the first setting, "Noiseless," no noise was injected in any layer. In the second setting, "InputNoise," a corrupted and noisy version of sentence embeddings were injected to the network. In the third setting, "EncoderNoise," noise was injected to an input layer and also to all encoder layers. In the fourth setting, "DecoderNoise," noise was injected to all layers of the unsupervised part of the network (input, encoder, and decoder). In the fifth setting, "FullNoise," noise was injected to all layers of the semi-supervised model (108), including layers of classifier 218. It was hypothesized that injecting noise to a network may lead to more robust model that achieves better performance on unseen data. The results in Table 1 above confirm this expectation. However, it appears that noise injection to the classifier part (FullNoise) is not very helpful, and that DecoderNoise was the best setting.

Turning to regularization, multiple regularization methods were attempted: "RegResidual," "L2Residual," and "NoRegResidual." With "RegResidual,", a residual model equipped with both L1 and L2 regularizers was used. With "L2Residual," a residual model equipped with L2 regularizer was used. With "NoRegResidual," a residual model without L1 and L2 regularizers was used. L1 and L2 regularizers were used for softmax weights to control them. L1 regularization tends to make the weights zero whereas L2 regularization tends to make them close to zero. Based on the experimental results in Table 1, when 500 labeled examples were used, using both L1 and L2 regularizers help since more limitation was put on weights when less data was available. But in case of 1000 labeled examples, there was less need to force weights to be zero—just keeping them relatively low was enough to achieve a good result.

Turning to residual connection selection, the only difference between FullNoise and RegResidual model is having residual connections in the RegResidual model. Adding residual connections help the network to remember forgotten important information over layers of the model (RSDA 220). Table 1 indicates that augmenting the model with residual connections improves the accuracy of the test set by 0.89% and 0.83% when 500 and 1000 labeled examples were used, respectively, which is a noticeable improvement. This jump in the performance of the model by just introducing residual connections demonstrates the effectiveness and capability of RSDA 220.

Turning to activation, the activation function in a network could be varied based on the task and the type of the datasets. Usually, ReLU performs very well for images whereas tan h performs better for textual data. The effects of different activation functions were studied as well. "RegResidual" is a residual model that uses the tan h activation function. "LinearRes" is a residual model that uses the linear activation function. "ReLURes" is a residual model that uses the ReLU activation function. "SigmoidRes" is a residual model that uses the Sigmoid activation function. According to Table 1, LinearRes performs worst among all models. SigmoidRes performs better than ReLURes because of its non-linearity. Textual data, such as word embeddings, present an n-dimensional space where both positive and negative range of real numbers are used, but ReLU and Sigmoid map their inputs to positive range of real numbers. Because of this limitation, better results were achieved in RegResidual that uses the tan h activation function.

Lastly, turning to input applied to classifier 218, various combinations of test cases were attempted:

SimpleIn: $(u \oplus v)$
AugProdIn: $(u \oplus v \oplus (u \odot v))$
AugAbsIn: $u \oplus v \oplus |u-v|$
AbsProdIn: $|u-v| \oplus (u \odot v)$
RegResidual: $u \oplus v \oplus |u-v| \oplus (u \odot v)$ In these test cases, u and v are the encoder inputs and $\oplus$ and $\odot$ denote concatenation and element-wise product, respectively. The results in Table 1 demonstrate the importance of $|u-v|$ as an input to the classifier. The results also indicate that the extracted sentence embeddings carry necessary information for the classifier since absolute difference of sentence embeddings noticeably assist the classifier to make a decision about the entailment of the given sentences. The $(u \odot v)$ term is not very helpful, especially in the absence of $|u-v|$. It just increases the complexity and ambiguity of the learning function. When using 1000 labeled examples, the network can resolve this ambiguity to gain a better accuracy.

Figure 7:
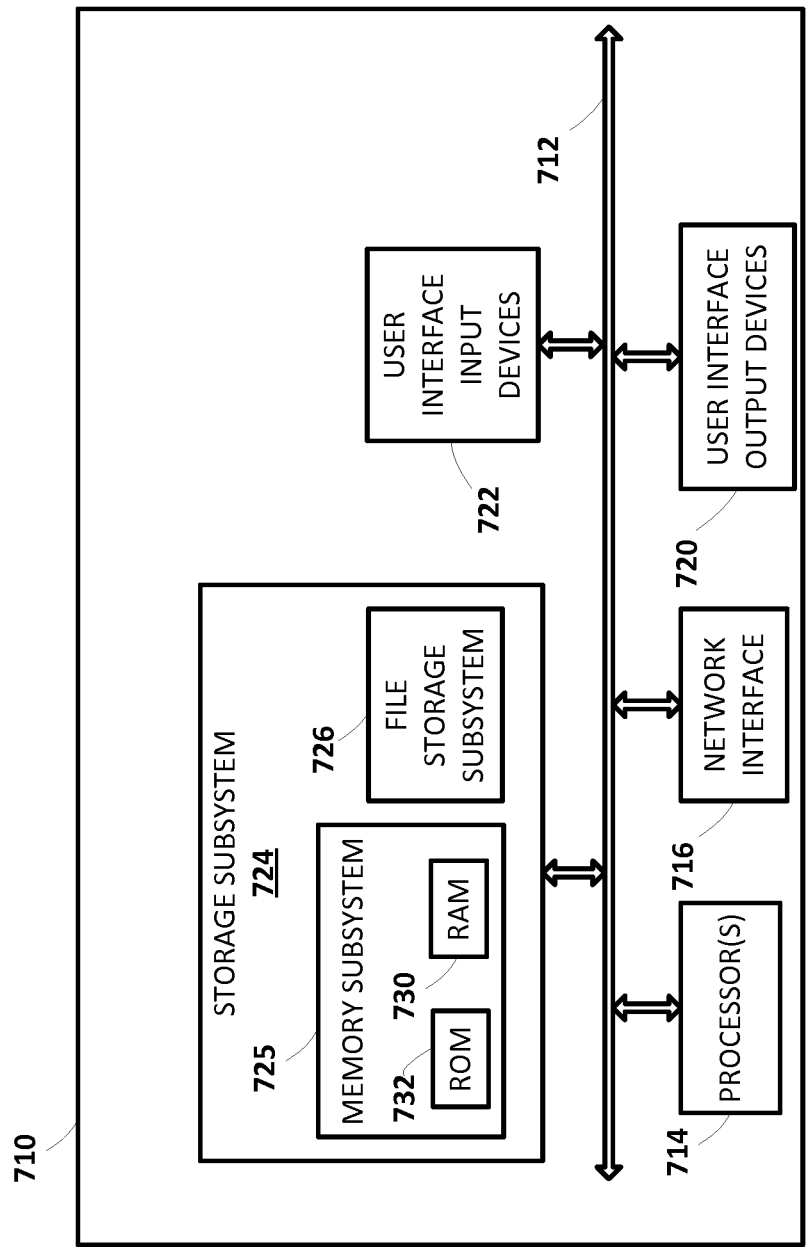
FIG. 7 depicts an example computer architecture, in accordance with various embodiments.

FIG. 7 is a block diagram of an example computer system 710. Computer system 710 typically includes at least one processor 714 which communicates with a number of peripheral devices via bus subsystem 712. As used herein, the term "processor" will be understood to encompass various devices capable of performing the various functionalities attributed to components described herein such as, for example, microprocessors, GPUs, FPGAs, ASICs, other similar devices, and combinations thereof. These peripheral devices may include a data retention subsystem 724, including, for example, a memory subsystem 725 and a file storage subsystem 726, user interface output devices 720, user interface input devices 722, and a network interface subsystem 716. The input and output devices allow user interaction with computer system 710. Network interface subsystem 716 provides an interface to outside networks and is coupled to corresponding interface devices in other computer systems.

User interface input devices 722 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 710 or onto a communication network.

User interface output devices 720 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 710 to the user or to another machine or computer system.

Data retention system 724 stores programming and data constructs that provide the functionality of some or all of the modules described herein. For example, the data retention system 724 may include the logic to perform selected aspects of FIGS. 1-5, as well as to implement selected aspects of method 600.

These software modules are generally executed by processor 714 alone or in combination with other processors. Memory 725 used in the storage subsystem can include a number of memories including a main random access memory (RAM) 730 for storage of instructions and data during program execution, a read only memory (ROM) 732 in which fixed instructions are stored, and other types of memories such as instruction/data caches (which may additionally or alternatively be integral with at least one processor 714). A file storage subsystem 726 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 726 in the data retention system 724, or in other machines accessible by the processor(s) 714. As used herein, the term "non-transitory computer-readable medium" will be understood to encompass both volatile memory (e.g. DRAM and SRAM) and non-volatile memory (e.g. flash memory, magnetic storage, and optical storage) but to exclude transitory signals.

Bus subsystem 712 provides a mechanism for letting the various components and subsystems of computer system 710 communicate with each other as intended. Although bus subsystem 712 is shown schematically as a single bus, alternative implementations of the bus subsystem may use multiple busses. In some embodiments, particularly where computer system 710 comprises multiple individual computing devices connected via one or more networks, one or more busses could be added and/or replaced with wired or wireless networking connections.

Computer system 710 can be of varying types including a workstation, server, computing cluster, blade server, server farm, or any other data processing system or computing device. In some embodiments, computer system 710 may be implemented within a cloud computing environment. Due to the ever-changing nature of computers and networks, the description of computer system 710 depicted in FIG. 7 is intended only as a specific example for purposes of illustrating some implementations. Many other configurations of computer system 710 are possible having more or fewer components than the computer system depicted in FIG. 7.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A method comprising:
   applying, as unlabeled training data across a trained embedding machine learning model, a first plurality of sentences to generate a plurality of sentence embeddings;
   applying, as input across an autoencoder machine learning model, the plurality of sentence embeddings to train the autoencoder machine learning model, wherein the autoencoder machine learning model includes one or more encoder layers and one or more decoder layers;
   applying, as labeled training data across one or more instances of an encoder machine learning model, a second plurality of sentences to generate a plurality of encoded embeddings, wherein the second plurality of sentences are associated with a corresponding plurality of labels, and wherein the encoder machine learning model includes the one or more encoder layers of the autoencoder machine learning model;
   applying, as labeled training data across a classifier, the plurality of encoded embeddings to generate output; and
   training the classifier based on the output and the plurality of labels to classify subsequent sentences with one or more of the plurality of labels.

2. The method of claim 1, wherein the embedding machine learning model comprises a skip-thoughts model.

3. The method of claim 1, wherein the one or more encoder layers comprise a sequence of multiple encoder layers, and the one or more decoder layers comprise a sequence of multiple decoder layers that mirror the sequence of multiple encoder layers.

4. The method of claim 3, wherein the autoencoder machine learning model includes one or more residual connections.

5. The method of claim 4, wherein the one or more residual connections include a residual connection between a last encoder layer of the sequence of multiple encoder layers and a last decoder layer of the sequence of multiple decoder layers.

6. The method of claim 1, wherein the embedding machine learning model comprises a convolutional neural network.

7. The method of claim 1, wherein the classifier comprises a multi-layer perceptron and a softmax layer.

8. The method of claim 1, wherein the first and second plurality of sentences comprise free form clinical notes, and the plurality of labels include a plurality of diagnoses associated with the free form clinical notes.

9. At least one non-transitory computer-readable medium comprising instructions that, in response to execution of the instructions by one or more processors, cause the one or more processors to perform the following operations:

applying, as unlabeled training data across a trained embedding machine learning model, a first plurality of sentences to generate a plurality of sentence embeddings;

applying, as input across an autoencoder machine learning model, the plurality of sentence embeddings to train the autoencoder machine learning model, wherein the autoencoder machine learning model includes one or more encoder layers and one or more decoder layers;

applying, as labeled training data across one or more instances of an encoder machine learning model, a second plurality of sentences to generate a plurality of encoded embeddings, wherein the second plurality of sentences are associated with a corresponding plurality of labels, and wherein the encoder machine learning model includes the one or more encoder layers of the autoencoder machine learning model;

applying, as labeled training data across a classifier, the plurality of encoded embeddings to generate output; and training the classifier based on the output and the plurality of labels to classify subsequent sentences with one or more of the plurality of labels.

10. The non-transitory computer-readable medium of claim 9, wherein the embedding machine learning model comprises a skip-thoughts model.

11. The non-transitory computer-readable medium of claim 9, wherein the one or more encoder layers comprise a sequence of multiple encoder layers, and the one or more decoder layers comprise a sequence of multiple decoder layers that mirror the sequence of multiple encoder layers.

12. The non-transitory computer-readable medium of claim 11, wherein the autoencoder machine learning model includes one or more residual connections.

13. The non-transitory computer-readable medium of claim 12, wherein the one or more residual connections include a residual connection between a last encoder layer of the sequence of multiple encoder layers and a last decoder layer of the sequence of multiple decoder layers.

14. The non-transitory computer-readable medium of claim 9, wherein the embedding machine learning model comprises a convolutional neural network.

15. The non-transitory computer-readable medium of claim 9, wherein the classifier comprises a multi-layer perceptron and a softmax layer.

16. The non-transitory computer-readable medium of claim 9, wherein the first and second plurality of sentences comprise free form clinical notes, and the plurality of labels include a plurality of diagnoses associated with the free form clinical notes.

17. A system comprising one or more processors and memory operably coupled with the one or more processors, wherein the memory stores instructions that, in response to execution of the instructions by one or more processors, cause the one or more processors to perform the following operations:

applying, as unlabeled training data across a trained embedding machine learning model, a first plurality of sentences to generate a plurality of sentence embeddings;

applying, as input across an autoencoder machine learning model, the plurality of sentence embeddings to train the autoencoder machine learning model, wherein the autoencoder machine learning model includes one or more encoder layers and one or more decoder layers;

applying, as labeled training data across one or more instances of an encoder machine learning model, a second plurality of sentences to generate a plurality of encoded embeddings, wherein the second plurality of sentences are associated with a corresponding plurality of labels, and wherein the encoder machine learning model includes the one or more encoder layers of the autoencoder machine learning model;

applying, as labeled training data across a classifier, the plurality of encoded embeddings to generate output; and training the classifier based on the output and the plurality of labels to classify subsequent sentences with one or more of the plurality of labels.

18. The system of claim 17, wherein the embedding machine learning model comprises a skip-thoughts model.

19. The system of claim 17, wherein the one or more encoder layers comprise a sequence of multiple encoder layers, and the one or more decoder layers comprise a sequence of multiple decoder layers that mirror the sequence of multiple encoder layers.

20. The system of claim 19, wherein the autoencoder machine learning model includes one or more residual connections.

21. A system comprising one or more processors and memory operably coupled with the one or more processors, wherein the memory stores instructions that, in response to execution of the instructions by one or more processors, cause the one or more processors to apply a semi-supervised model to a model input, applying the semi-supervised model comprising applying the model input across a trained embedding machine learning model, to generate a sentence embedding;

applying, as an input across a trained autoencoder machine learning model, the sentence embedding to generate an encoded embedding, wherein the autoencoder machine learning model includes one or more encoder layers;

applying, across a classifier, the encoded embedding to generate output.

* * * * *